US008980951B2

(12) United States Patent
Vediyappan et al.

(10) Patent No.: US 8,980,951 B2
(45) Date of Patent: Mar. 17, 2015

(54) SESQUITERPENES FOR ANTIFUNGAL APPLICATIONS (71) Applicant: Kansas State University Research Foundation, Manhattan, KS (US)

(72) Inventors: Govindsamy Vediyappan, Manhattan, KS (US); Duy H. Hua, Manhattan, KS (US)

(73) Assignee: Kansas State University Research Foundation, Manhattan, KS (US)

(*) Notice: Subject to any disclaimer, the term of this patent is extended or adjusted under 35 U.S.C. 154(b) by 0 days.

(21) Appl. No.: 14/159,525

(22) Filed: Jan. 21, 2014

(65) Prior Publication Data

US 2014/0135404 A1 May 15, 2014

Related U.S. Application Data (63) Continuation-in-part of application No. PCT/US2012/047658, filed on Jul. 20, 2012.

(60) Provisional application No. 61/510,439, filed on Jul. 21, 2011.

(51) Int. Cl.
| | |
|---|---|
| *A01N 33/00* | (2006.01) |
| *A61K 31/13* | (2006.01) |
| *A61K 31/16* | (2006.01) |
| *A01N 35/00* | (2006.01) |
| *A61K 31/12* | (2006.01) |
| *A01N 31/00* | (2006.01) |
| *A61K 31/045* | (2006.01) |
| *A01N 27/00* | (2006.01) |
| *A61K 31/01* | (2006.01) |
| *A61K 31/015* | (2006.01) |
| *C07C 33/14* | (2006.01) |
| *A01N 31/06* | (2006.01) |

(52) U.S. Cl.
CPC ............... *C07C 33/14* (2013.01); *A61K 31/045* (2013.01); *A01N 31/06* (2013.01)
USPC ........... 514/579; 514/678; 514/724; 514/729; 514/763

(58) Field of Classification Search
USPC ............. 514/729, 579, 678, 724, 762, 763
See application file for complete search history.

(56) References Cited

U.S. PATENT DOCUMENTS

| | | | |
|---|---|---|---|
| 3,561,444 | A | 2/1971 | Boucher |
| 3,703,173 | A | 11/1972 | Dixon |
| 4,624,251 | A | 11/1986 | Miller |
| 4,635,627 | A | 1/1987 | Gam |
| 4,962,091 | A | 10/1990 | Eppstein et al. |
| 5,917,084 | A | 6/1999 | Jiang |
| 6,140,360 | A | 10/2000 | Takahashi et al. |

FOREIGN PATENT DOCUMENTS

| | | |
|---|---|---|
| WO | 9407529 | 4/1994 |
| WO | 9953911 | 10/1999 |

OTHER PUBLICATIONS

Derita et al. ("Importance of the C9 absolute configuration for the antifungal activity of natural and semisynthetic sesquiterpenes" Research, Development and Evaluation, Proceedings of the International Conference on Antimicrobial Research, Valladolid, Spain, Nov. 3-5, 2010, 373-375).*
The International Search Report and Written Opinion dated Aug. 30, 2012 in corresponding PCT/US2012/47658 filed Jul. 20, 2012.
Hua, D. J. Org. Chem. 2004, 6065-6078, 69.

* cited by examiner

*Primary Examiner* — Yong Chong
(74) *Attorney, Agent, or Firm* — Hovey Williams LLP (57) ABSTRACT Bicyclic sesquiterpene compounds exhibiting antifungal characteristics are formulated into antifungal compositions for use in the treatment of fungal infections in humans, animals, and plants. Particularly, sesquiterpene alcohols derived from drimane have been discovered to possess broad-spectrum antifungal characteristics. Exemplary antifungal sesquiterpene compounds include albicanol and drimenol, which have been shown effective against a number of pathogenic fungi.

8 Claims, 4 Drawing Sheets

SESQUITERPENES FOR ANTIFUNGAL APPLICATIONS

RELATED APPLICATION

This application is a continuation-in-part of International Application No. PCT/US2012/047658, filed Jul. 20, 2012, which claims the benefit of U.S. Provisional Patent Application No. 61/510,439, filed Jul. 21, 2011, both of which are incorporated by reference herein in their entireties.

BACKGROUND OF THE INVENTION

1. Field of the Invention

The present invention is generally directed toward antifungal compositions and methods of treating fungal infections with the same. Particularly, the antifungal composition comprises, as an active ingredient, one or more bicyclic sesquiterpene compounds, and specifically drimane derivatives. The antifungal composition can be formulated to include one or more pharmaceutically acceptable carriers for the sesquiterpene compound(s). The composition can also be administered to animals and humans through various means, such as topically, in the treatment of pathogenic fungal infections.

2. Description of the Prior Art

Fungi have emerged in the last two decades as major causes of human disease costing the U.S. health care system between $3-5 billion annually. As people are using immunosuppressive and antimicrobial chemotherapies increasingly, various types of fungal infections including superficial and life threatening invasive infections, are on the rise. *C. albicans* is a major fungal pathogen affecting all ages and the fourth leading cause of nosocomial bloodstream infections in the U.S. *C. albicans* and other *Candida* spp. cause mucosal, disseminated and invasive candidiasis, especially among patients who are immune-compromised or hospitalized with serious underlying diseases. The overall mortality for invasive diseases caused by *Candida* spp. and *Aspergillus* spp. is around 50% despite new diagnostic and therapeutic strategies. While there are more than 150 species of *Candida*, about 15 species are recognized as frequent human pathogens including: *C. albicans, C. glabrata, C. krusei, C. tropicalis,* and *C. parapsilosis*. Among these, *C. albicans* is by far the most common species isolated from humans and is a frequent denizen of the oropharynx, mucosal surfaces, gastrointestinal and genitourinary tracts.

Other fungal pathogens such as *Cryptococcus* and *Aspergillus* spp. also contribute significant morbidity and mortality. In the developing world, there are ~1 million cases of cryptococcal disease per year, resulting in 675 000 deaths (Park, et. al. AIDS 2009, 23, 525-530). *Cryp. neoformans* is an opportunistic fungal pathogen that causes meningitis in immune-compromised individuals. Often found in soils contaminated with bird feces, *C. neoformans* enters its host through the lungs via inhalation of spores. Some of the cryptococcal species are hypervirulent and have recently drawn considerable public attention due to their causative role in the cryptococcosis outbreak throughout the Pacific Northwest.

*Aspergillus* spp. are ubiquitous molds found widely in the environment as saprophytes and produce microscopic spores or conidia which upon inhalation, cause invasive pulmonary disease. In immune-compromised patients such as those undergoing hematopoietic stem cell transplantation, solid organ transplantation, or receiving chemotherapeutic agents or immunomodulator agents, invasive aspergillosis remains the most important cause of infection-related mortality. Among several species of *Aspergillus*, *A. fumigatus* and *A. flavus* are frequent pathogens.

Dermatophytes are another group of keratinophilic pathogenic fungi that cause a variety of infections in humans and animals. Some of these fungi include *Trichophyton tonsurans* (scalp ringworm), *T. equinum*, and *Microporum gypseum* (gardener's ringworm). Emerging fungal disease such as zygomycosis is life-threatening particularly during the aftermath of natural calamities (e.g., tsunamis, hurricanes, and tornados).

Allergic fungal syndromes are increasingly recognized. There are increasing reports of dermatophytes and rare molds (e. g. *Bipolaris, Fusarium* and *Curvularia*) that cause devastating infections in a range of patients (Denning and Hope, Trends Micro. 2010, 18, 195-204).

Because fungi are eukaryotes, the development of antifungal therapeutics that are non-toxic to humans is challenging. In the last 30 years, only one new class of antifungal compounds ($\beta$-glucan synthase inhibitor, the echinocandins) has been introduced into clinical practice. Although this drug is an important addition, it has a number of limitations including ineffectiveness against *Cryptococcus* sp. and poor oral bioavailability. Other currently available antimycotics contain similar limitations with respect to efficacy against certain fungi, bioavailability, and the development of antifungal resistance by fungal pathogens.

SUMMARY OF THE INVENTION

The present invention overcomes the above challenges by providing, according to one embodiment, an antifungal composition comprising, consisting of, or consisting essentially of one or more bicyclic sesquiterpene compounds dispersed in a pharmaceutically acceptable carrier. In particular embodiments, the one or more sesquiterpene compounds comprise derivatives of drimane, and even more particularly comprise bicyclic sesquiterpene alcohols.

In another embodiment, methods for treating a fungal infection in an animal or human body are provided which comprise, consist of, or consist essentially of the step of administering to the animal or human a composition comprising a therapeutically effective amount of one or more bicyclic sesquiterpene compounds. Methods according to the present invention are useful to control a number of fungi including many pathogenic fungi such as *Candida* spp., *Cryptococcus* spp., *Aspergillus* spp., and dermatophytes.

In still another embodiment of the present invention, methods of protecting plants from fungi are provided. These methods generally comprise applying to the plant an antifungal composition comprising, consisting of, or consisting essentially of an amount of one or more bicyclic sesquiterpene compounds effective to inhibit the growth of or kill one or more species of fungi infecting the plant.

DETAILED DESCRIPTION OF THE PREFERRED EMBODIMENT

Figure 1:
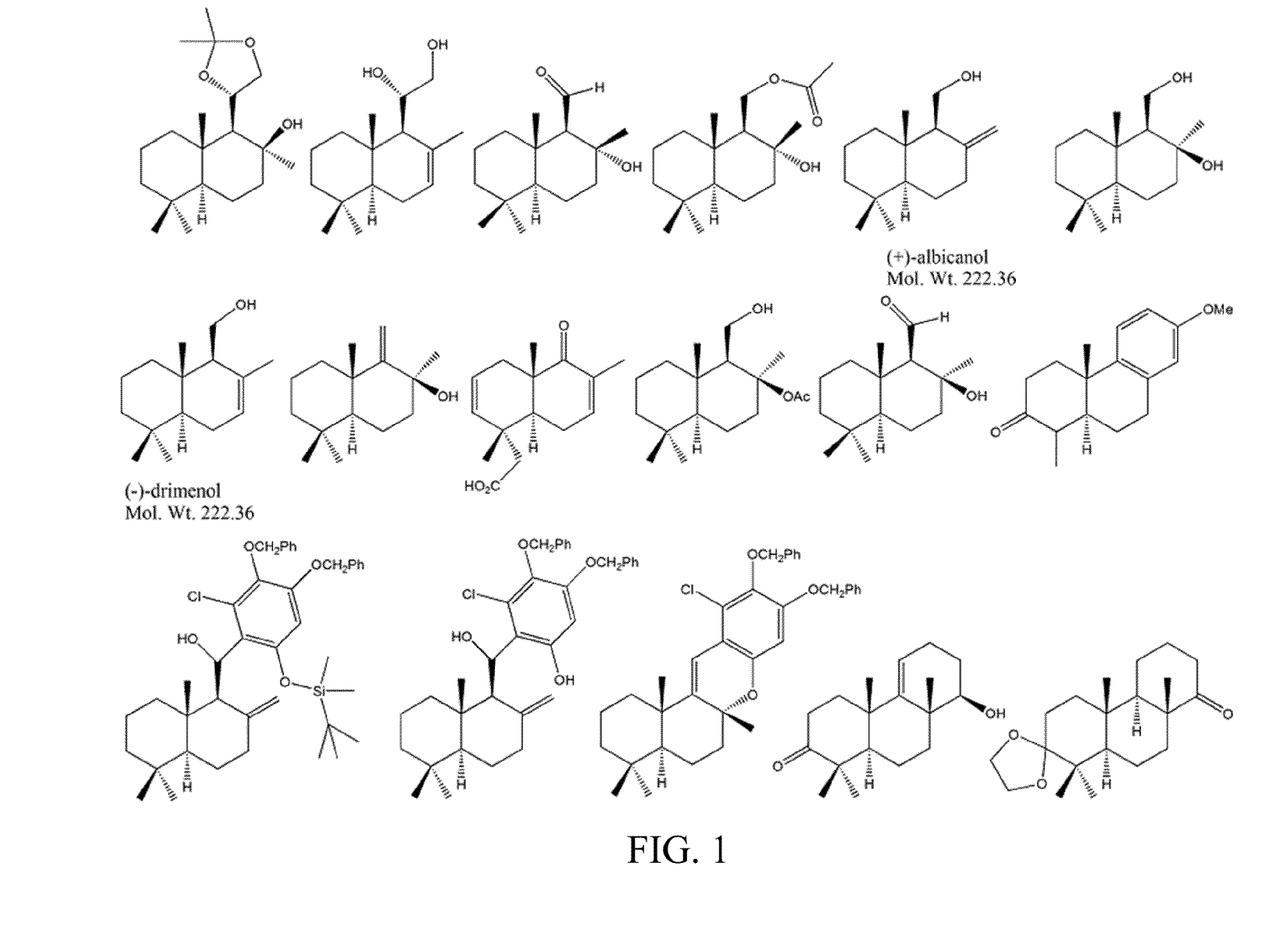
FIG. 1 illustrates a number of drimane-derived sesquiterpene compounds, including albicanol and drimenol.
Figure 4:
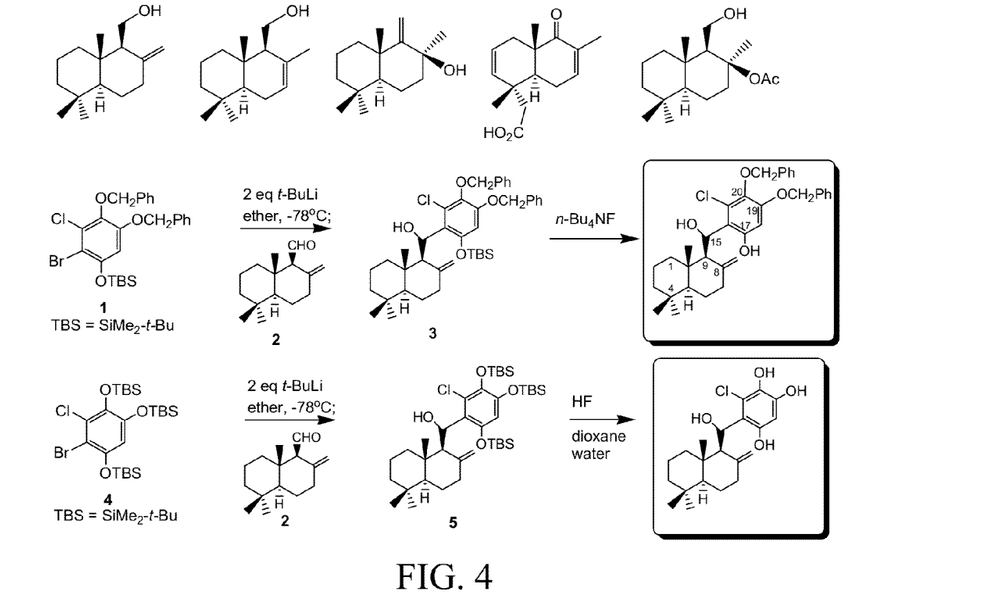
FIG. 4 illustrates additional drimane-derived sesquiterpene compounds including a reaction scheme for synthesizing certain particular compounds.
Figure 5:
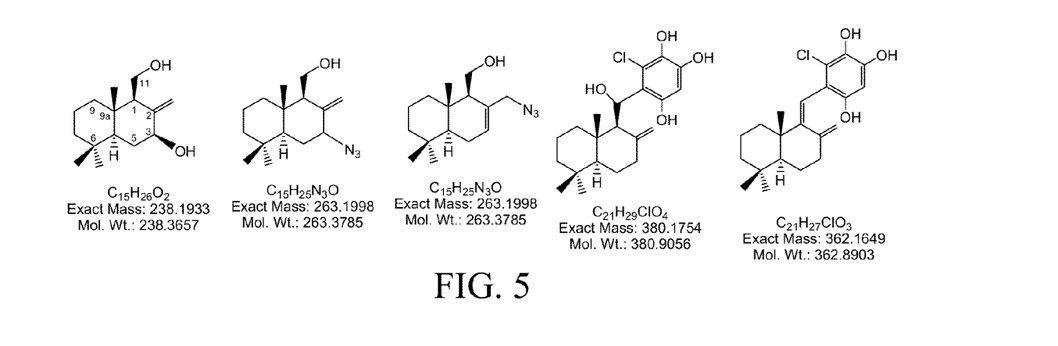
FIG. 5 illustrates additional drimane-derived sesquiterpene compounds.

One aspect of the present invention involves the synthesis of new compounds that exhibit fungicidal activity. Particularly, these compounds are sesquiterpene compounds. Sesquiterpenes are a class of terpenes that comprise three isoprene units and have the molecular formula $C_{15}H_{24}$. Sesquiterpenes may be acyclic or cyclic. When cyclic, the sesquiterpenes may be monocyclic or contain multiple rings, including many unique combinations. Biochemical modifications such as oxidation or rearrangement produce the related sesquiterpenoids. In certain embodiments of the present invention, the sesquiterpene compounds are bicyclic and comprise derivatives of drimane (structure below), in which certain of the methyl groups appended to the bicyclic ring structure have been modified or replaced with other substituent groups, especially hydrophobic and hydrophillic groups. Exemplary drimane derivative compounds prepared according to the present invention are depicted in FIGS. 1, 4, and 5.

Drimane

In some embodiments, the bicyclic sesquiterpene compounds comprise sesquiterpene alcohols, especially drimane-type sesquiterpene alcohols. In particular embodiments according to the present invention, the bicyclic sesquiterpene compounds are selected from the group consisting of albicanol, drimenol and mixtures thereof. Even more specifically, the bicyclic sesquiterpene compounds comprise the enantiomers (+)-albicanol, (−)-drimenol, or mixtures thereof, whose chemical structures are noted below.

(+)-albicanol          (−)-drimenol

Albicanol and drimenol can also be modified so as to provide derivatives having improved physical characteristic suitable for formulation into pharmaceutical compositions. Particularly, hydrophilic and hydrophobic groups can be introduced onto the compounds at C2 and C4, in the case of drimenol and at C2 and C3 in the case of albicanol. In certain embodiments, the bicyclic sesquiterpene alcohols are to be selected from the group consisting of:

wherein $R^1$ is $CH_2$, CHR', S, NHR', or O,
wherein $R^2$ is H, OH, OR', =O, $CH_2OH$, CHO, $CO_2H$, $CH=CH_2$, $CH_3$, $CH_2CH_3$, $N_3$, $C_3H_7$, or $NH_2$
wherein $R^3$ is $CH_3$, NHR', $CH_2N_3$, or OR', and
wherein $R^4$ is H, $CH_2OH$, CHO, $CO_2H$, $CH=CH_2$, $CH_3$, $CH_2CH_3$, $C_3H_7$, or $CH_2NHR'$,
wherein R' is alkyl or aryl.

Figure 2:
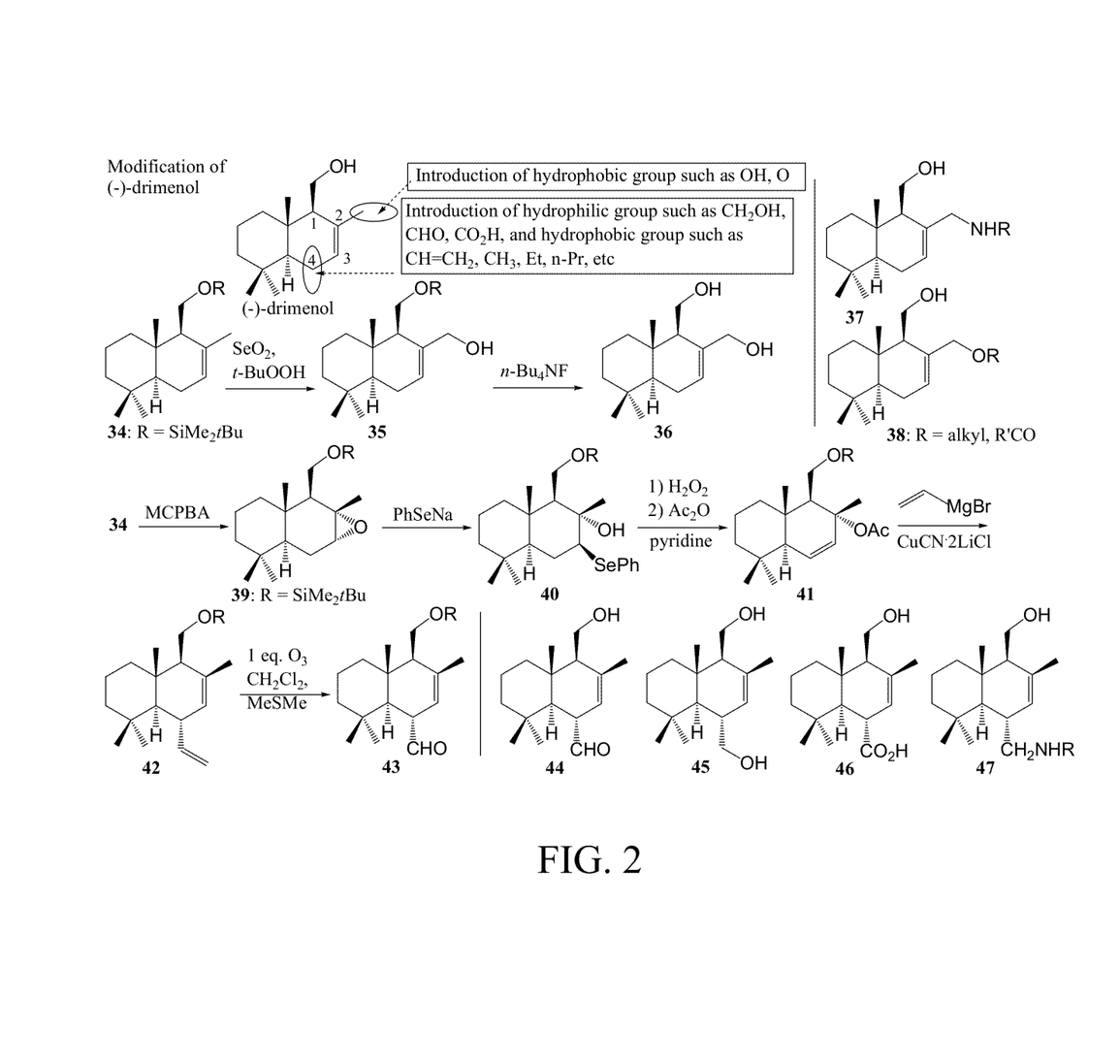
FIG. 2 illustrates a reaction scheme for synthesizing drimenol derivative compounds.

An exemplary synthesis scheme for modification of (−)-drimenol is given in FIG. 2. Modification of C4 can be conducted by a regioselective epoxidation followed by epoxide opening with phenylselenyl ion and oxidative elimination affording allylic alcohol. The allylic alcohol function allows further functional group manipulation to introduce C4 substituents. Hence, epoxidation of compound 34 with m-chloroperoxybenzoic acid (MCPBA) gives epoxide 39. The oxidant should approach the C2 double bond of compound 34 from the alpha face opposite to the C1-silyloxymethyl and C8a-methyl. Epoxide ring opening of 39 with phenylselenyl ion, generated from diphenyl diselenide and sodium borohydride, gives selenide 40, in which the selenide ion attacks the epoxide ring at the less hindered carbon C3 from the backside.

Oxidation of the selenide moiety of compound 40 with hydrogen peroxide gives selenyl oxide which undergoes rapid β-elimination affording C3, C4 alkene. Acetylation of the allylic alcohol with acetic anhydride in pyridine produces acetate 41. $S_N2'$ displacement of allylic acetate 41 with vinyl magnesium bromide in the presence of a catalytic amount of CuCN.2LiCl provides compound 42. Presumably, the displacement reaction takes place with retention since the beta-face is hindered. However, if an inversion takes place, the beta-oriented vinyl compound will be used in the sequence of reactions described below. The less hindered exo-vinylic moiety of compound 42 is more reactive than the substituted endo alkenyl moiety, hence it can be selectively oxidized with 1 equivalent of ozone in dichloromethane at −78° C. followed by reduction with dimethyl sulfide to give aldehyde 43.

Various drimenol derivatives containing a hydrophilic group at C4 are readily synthesized from compound 43. Hence removal of the silyl ether group of 43 will furnish drimenol derivative 44, which is reduced with sodium borohydride to give diol 45. Oxidation of aldehyde 43 with silver (I) oxide followed by the removal of the silyl ether protecting group gives carboxylic acid 46. Reduction amination reaction of aldehyde 43 with various primary amines and sodium cyanoborohydride followed by removal of the silyl ether group gives amine 47. Hydrophobic groups can be introduced by the alkylation of the hydroxyl functional group (obtained from the reduction of 43 with sodium borohydride) with sodium hydride and alkyl halide followed by n-Bu$_4$NF.

Note that in these two compounds C2 is bonded either with $R^1$ or with C3 through an unsaturated bond. Without wishing to be bound by any particular theory, it is suspected that the fungicial activity of these particular drimane-derived, bicyclic sesquiterpene compounds is due at least in part to the unsaturated double bond involving C2 (to which $R^1$ is appended) and the hydroxy-functional group appended to C1.

Turning to FIG. 4, various other drimane-derived sesquiterpene compounds are shown. The final molecule of the first reaction scheme of FIG. 4 was synthesized in optically pure form from the treatment of aryl halide 1 with tert-butyllithium in diethyl ether at −78° C. followed by the addition of aldehyde 2 and removal of the silyl ether protecting group with tetra-n-butylammonium fluoride. Similarly, the final molecule of the second reaction scheme was synthesized from the coupling of aryl halide 4 and aldehyde 2 followed by deprotection with HF.

FIG. 5 provides further exemplary synthesized drimane-derived sesquiterpene compounds in accordance with the present invention. All compounds shown in FIGS. 1, 3, and 4 have been synthesized.

The sesquiterpene compounds described above, especially the bicyclic sesquiterpene alcohols, may be formulated into antifungal compositions. Generally, this involves dispersing a therapeutically effective amount of one or more sesquiterpene compounds described above in a pharmaceutically acceptable carrier.

As used herein, the term "pharmaceutically acceptable" means a carrier, diluent, excipient, and/or salt that is compatible with the other ingredients of the formulation, and not deleterious to the recipient thereof.

As used herein, the term "therapeutically effective amount" refers to an amount of one or more sesquiterpene compounds described herein that is of sufficient quantity to inhibit the growth of or reduce the quantity of one or more fungi in a patient, animal or human, receiving the composition.

The antifungal compositions can be formulated for any kind of mode of delivery to the patient including oral, topical, by inhalation, intravenous, or parenteral delivery. Thus, depending upon chosen mode of delivery, the antifungal composition can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone.

Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For oral administration, the one or more sesquiterpene compounds may be present as a powder, a granular formulation, a solution, a suspension, an emulsion or in a natural or synthetic polymer or resin for ingestion of the active ingredients from a chewing gum. The active sesquiterpene compounds may also be presented as a bolus, electuary or paste.

The formulations may, where appropriate, be conveniently presented in discrete unit dosage forms and may be prepared by any of the methods well known to the pharmaceutical arts including the step of mixing the therapeutic compounds with liquid carriers, solid matrices, semi-solid carriers, finely divided solid carriers or combinations thereof, and then, if necessary, introducing or shaping the product into the desired delivery system. The total amount of the one or more sesquiterpene compounds in such formulations can be between about 0.01% to about 99%, between about 0.1% to about 90%, between about 0.5% to about 50%, or between about 1% to about 10% by weight based on the total weight of the composition.

Tablets or caplets containing one or more sesquiterpene compounds can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing one or more sesquiterpene compounds can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more sesquiterpene compounds of the present invention are designed to resist disintegration in the stomach and dissolve in the more neutral to alkaline environment of the duodenum. Orally administered therapeutic compounds of the present invention can also be formulated for sustained release. In this case, the compounds can be coated, micro-encapsulated (see WO 94/07529, and U.S. Pat. No. 4,962,091), or otherwise placed within a sustained delivery device.

A sustained-release formulation can be designed to release the one or more sesquiterpene compounds, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

One or more sesquiterpene compounds of the invention can also be formulated as elixirs or solutions for convenient oral administration or as solutions appropriate for parenteral administration, for instance by intramuscular, subcutaneous, intraperitoneal or intravenous routes. A pharmaceutical formulation of a therapeutic sesquiterpene compound can also take the form of an aqueous or anhydrous solution or dispersion, or alternatively the form of an emulsion or suspension or salve.

Thus, one or more sesquiterpene compounds may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The sesquiterpene compounds and other ingredients may form suspensions, solutions, or emulsions in oily or aqueous vehicles, and may contain formulatory agents such as suspending, stabilizing and/or dispersing agents. Alternatively, the active sesquiterpene compounds and other ingredients may be in powder form, obtained by aseptic isolation of sterile solid or by lyophilization from solution, for constitution with a suitable vehicle, e.g., sterile, oxygen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name DOWANOL, polyglycols and polyethylene glycols, C1-C4 alkyl esters of short-chain acids, ethyl or isopropyl lactate, fatty acid triglycerides such as the products marketed under the name MIGLYOL, isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

In some embodiments, the one or more sesquiterpene compounds are formulated as a fungicide, which is administered topically or to mucosal surfaces such as the vagina, the rectum, eyes, nose and the mouth. For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the one or more sesquiterpene compounds can be delivered via patches or bandages for dermal administration. Alternatively, the one or more sesquiterpene compounds can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Topical applications may also comprise an adjuvant. Compositions for topical application to skin may include an adjuvant, solvent, or co-solvent to assist the one or more sesquiterpene compounds with penetrating the outer dermal layers. An exemplary adjuvant, solvent, or co-solvent is dimethyl sulfoxide (DMSO). The one or more sesquiterpene compounds generally comprise at least about 0.0003%, 0.0005%, or 0.001% by weight of the total weight of the formulation. In other embodiments, the one or more sesquiterpene compounds are generally present in an amount of about 0.0003% to about 5%, about 0.0005% to about 1%, about 0.001% to about 0.75%, or about 0.005% to about 0.5% by weight of the total weight of the formulation.

Drops, such as eye drops or nose drops, may be formulated with one or more of the sesquiterpene compounds in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The one or more sesquiterpene compounds of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of infection. Any statistically significant attenuation of one or more symptoms of the infection that has been treated pursuant to the method of the present invention is considered to be a treatment of such infection within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in Aerosols and the Lung, Clarke, S. W. and Davia, D. eds., pp. 197-224, Butterworths, London, England, 1984).

One or more sesquiterpene compounds of the present invention can also be administered in an aqueous solution when administered in an aerosol or inhaled form. Thus, other aerosol pharmaceutical formulations may comprise, for example, a physiologically acceptable buffered saline solution containing between about 0.01 mg/mL and about 100 mg/mL of one or more of the sesquiterpene compounds of the present invention specific for the indication or disease to be treated. Dry aerosol in the form of finely divided solid sesquiterpene particles that are not dissolved or suspended in a liquid are also useful in the practice of the present invention. In certain embodiments, the sesquiterpene compounds may be formulated as dusting powders and comprise finely divided particles having an average particle size of between about 1 and 5 μm, alternatively between 2 and 3 μm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the one or more sesquiterpene compounds of the invention can be conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

The one or more sesquiterpene compounds of the present invention may also be used in combination with one or more known therapeutic agents, for example, a pain reliever; an antiviral agent; an antibacterial agent; an anti-cancer agent; an anti-inflammatory agent; an antihistamine; a bronchodilator and appropriate combinations thereof, whether for the conditions described or some other condition.

According to another embodiment of the present invention, the sesquiterpene compounds and pharmaceutical composition described above can be used to treat fungal infections in an animal or human body. Compounds according to the present invention, especially the above-referenced drimane derivatives, can be used as broad-spectrum antifungal agents to treat numerous types of fungal infections. In particular embodiments, the sesquiterpene compounds used in methods of treating a fungal infection in an animal or human are selected from the group consisting of albicanol and drimenol, and particularly the enantiomers (+)-albicanol and (−)-drimenol.

The sesquiterpene compounds or compositions comprising one or more sesquiterpene compounds as active ingredients may be delivered by a number of means including oral, topical, inhalation, intravenous, or parenteral delivery. Irrespective of the selected mode of delivery, methods as described herein comprise delivery of a therapeutically effective amount of the one or more sesquiterpene compounds to the animal or human body. Precise dosage amounts may be dependent upon a number of variables including severity of the infection, body weight, the affected body area, and type of fungus being treated.

The antifungal compositions comprising one or more sesquiterpene compounds can be used to treat infections causes by a wide number of pathogenic fungi including *Candida* spp., *Cryptococcus* spp., and *Aspergillus* spp., and dermatophytes. More specifically, the fungal infection may be caused by a member selected from the group consisting of *C. albicans, C. glabrata, C. krusei, C. tropicalis, C. parapsilosis, Cryp. neoformans, A. fumigatus, A. nidulans, A. flavus, Trichophyton equinum, T. tonsurans, Microsporum gypseum* and *M. cani*.

In certain embodiments according to the present invention, it has been discovered that albicanol, drimenol and derivatives thereof are highly efficacious in the control of fungi including fluconazole resistant *C. alibcans, Cryptococcus* sp. and *Aspergillus* sp. at minimum inhibitory concentrations (MIC) between about 25 to about 50 µg/ml. For dermatophyte fungi, the MIC has been determined to be between about 5 to about 15 µg/ml. Moreover, testing has shown that cells treated with these compounds do not exhibit resistance development.

Under certain in vitro growth conditions, and as described in further detail hereunder, chemically synthesized (+)-albicanol and (−)-drimenol are fungicidal to various species of *Candida*, including the drug resistant *C. albicans* clinical strains, at concentrations ranging from about 50 to about 100 µg/ml. Also, albicanol and drimenol exhibit an effective fungal concentration-50 ($EC_{50}$) values against various fungi of between about 5 to about 30 µg/ml, and a cytotoxic inhibitory concentration ($IC_{50}$) value against human intestine epithelial cell lines (Int. 407) of about 50 µg/ml using Promega's cell viability assay kit. The selective index, or therapeutic index (Int-407 $IC_{50}$/fungal $EC_{50}$), of albicanol and drimenol ranged from between about 2 to about 6. The higher the therapeutic index, the greater is the efficacy of the compound against the fungi strain.

Given the broad-spectrum fungicidal properties of sesquiterpene compounds according to the present invention, the sesquiterpene compounds may be used to protect plants from pathogenic fungi as well. The sesquiterpene compounds may be used in controlling plant pathogenic fungi such as wheat rust pathogens, pecan scab, mildews and molds that affect agriculture, food storage fungi, including aflotoxin-producing fungi (*Aspergillus*, etc.), cattle food spoiling fungi, and fruit rot fungi. In such methods, at least one sesquiterpene compound, or composition formulated with the sesquiterpene compound(s), is applied to the plant in an amount effective to inhibit the growth of or kill one or more fungi that may be infecting the plant. Formulated compositions including one or more sesquiterpene compounds may comprise any adjuvants or carriers known to those skilled in the area of delivery of active agents to plant, including those materials mentioned previously.

EXAMPLE

The following example sets forth the results of a study of the fungicidal activity of albicanol and drimenol. It is to be understood, however, that this example is provided by way of illustration and nothing therein should be taken as a limitation upon the overall scope of the invention.

Synthesis

Albicanol and drimenol were prepared in optically pure form from a sequence of reactions starting from commercially available (+)-sclareolide as illustrated below (Hua et al., J. Org. Chem. 2004, 69, 6065-6078).

(-)-drimenol

Activity of Albicanol and Drimenol on Various Pathogenic Fungi

Synthetic pure albicanol and drimenol were dissolved in DMSO (10 mg/ml as stock solution) and used to determine their antifungal activities (minimum inhibitory concentration, MIC) against various fungi according to the microdilution assay of Clinical and Laboratory Standards Institute (CLSI (2008). Reference method for broth dilution antifungal susceptibility testing of yeasts and filamentous fungi: Approved Standard-Third Edition. Clinical and Laboratory Standards Institute 940 West Valley Road, Wayne, Pa. CLSI document M27-A3 & M38-A28. An initial assay had confirmed the antifungal activity of albicanol and drimenol; therefore, the susceptibility assay was extended to other pathogenic fungi including fluconazole resistant *C. albicans*, various species of candida, *Cryptococcus, Aspergillus* and a dermatophyte fungus.

Yeast cells or conidia (for filamentous fungi) were suspended in RPMI 1640 (with 50 mM glucose) medium to a final concentration of $10^4$ cfu/ml and distributed in a 96-well microplate to a total volume of 100 µl/well. Albicanol and drimenol were added into the wells and serial dilutions (broad or narrow range) with replicates were made, and wells with or without DMSO served as controls. Plates were incubated without shaking at 37° C. for 24-48 h for yeasts and 30° C. for 4 days for filamentous fungi (*Aspergillus* and *Trichophyton* sp). The MIC was defined as the lowest compound concentration at which no growth occurred, as determined visually and by $OD_{600}$ measurement (or microscopically, inverted). As a positive control, amphotericin B (AMB) (1 µg/ml) was also included in parallel. Cytotoxicity of albicanol and drimenol was determined using human intestinal epithelial cell lines (Int-407) by utilizing cell viability assay kit of Promega. Inhibitory concentration-50 ($IC_{50}$) for human cell lines and fungal cells were also calculated and are provided in Table 1.

TABLE 1

Summary of in vitro activities of albicanol and drimenol for selected fungi

| | | $MIC^a$ (µg/ml) Albicanol (drimenol) | Fungal $EC_{50}{}^b$ (µg/ml) | Selective Index (Int-407 $IC_{50}{}^c$/ fungal $EC_{50}$) |
|---|---|---|---|---|
| Albicanol (or drimenol) | *C. albicans* SC5314 | 50 (40) | 25 (22) | 2 (2.27) |
| | *C. albicans* Day 185 | 40 (25) | 22 (12) | 2.27 (4.16) |
| | *Cryp. neoformans* | 40 (30) | 22 (16) | 2.27 (3.12) |
| | *T. equinum* | 15 (5) | 8 (8) | 6.25 (6.25) |

$^a$Minimum inhibitory concentration determined according to CLSI methods at which no fungal growth was detected.
$^b$50% fungal inhibitory concentration due to compounds
$^c$50% cytotoxic concentration. Human intestine epithelial cell line (Int-407) was used to determine cyctotoxicity of albicanol and drimenol using Promega's cell viability assay kit. $IC_{50}$ of Int-407 cells exposed to albicanol or drimenol for 24 h was calculated around 50 µg/ml.

Since fungal cell physiology, growth medium or condition and physiochemical properties can affect the antifungal susceptibility of compounds, tests were conducted in different growth media, such as synthetic complete yeast nitrogen base (YNB), yeast peptone dextrose (YPD) media, and at 30° C.

Test were conducted on *A. nidulans, C. albicans, C. albicans* 95-158 Flu-R (fluconazole resistant strain), *Cryp. neomormans, Candida krusei*, and *C. glabrata*. Cells were exposed to albicanol and drimenol at concentrations of 50 µg/ml for 24 h, or 100 µg/ml for 48 h. To determine viability of the treated fungal cells, small volumes (1-5 µg/ml) of mixed cell suspensions were removed from wells and spotted on YPD agar medium. The agar plates were incubated at 30° C. for 24-72 h and the growth of fungi were recorded. Growths of yeasts or filamentous fungi on YPD agar occurred in 24 h and 48-96 h, respectively. The results from these tests clearly suggest that drimenol is fungicidal at 100 µg/ml (minimum fungicidal concentration, MFC) to all the fungi tested, which agrees with microscopic observation of swollen cells and their lysis due to drimenol exposure. Similar results were also from albicanol treated fungi. Even though, the broad range concentration tested is far less as compared to AMB (5-50 fold), it is believed that the true MFC value will be less than 100 µg/ml. Further, resistance to albicanol or drimenol was not observed in treated fungi after 72 h exposure indicating either the compounds act through multiple mechanisms or act via a pathway that cannot permit resistance development. Testing also showed that the bioactivities of albicanol and drimenol were not affected by the presence of amines or YPD medium.

Mode of Action (MOA) of Albicanol and Drimenol

As an initial step to understand the molecular mechanisms of albicanol and drimenol in fungal growth inhibition, genome-wide fitness profiling of barcoded homozygous non-essential and heterozygous essential mutants of *Saccharomyces cerevisiae* was performed using the yeast TAG4 microarray technology. Since *S. cerevisiae* is closely related to *C. albicans* and commonly used in antifungal drug discovery as well as its complete mutant collection being readily available, this yeast resource was used for mode of action (MOA) analysis. The $IC_{50}$ values of albicanol and drimenol for *C. albicans* and *S. cerevisiae* were determined in yeast growth (YPD) condition. Next, pooled mutant collections were grown in the presence or absence of compounds for 20-generations, barcodes from genomic DNA were amplified and relative strain abundance was quantified based on microarray signals. This haploinsufficiency profiling assay identifies drugs that target gene products essential for growth, based on the premise that lowering copy number of the target gene sensitizes the corresponding heterozygous deletion strain to the drug. At 20% growth inhibitory concentration for drimenol, 34 strains/ genes at the log ratio of >1.5 was depleted. These drug-induced sensitive strains are involved in various cellular processes such as transcription, amino acid biosynthesis, protein complex assembly or transport, cell wall organization and biosynthesis, chromatin remodeling and vacuolar functions. Thus it was concluded that both albicanol and drimenol affect multiple cellular processes in fungi and hence are fungicidal.

Cytotoxic and Antifungal Activities of Albicanol and Drimenol

Figure 3:
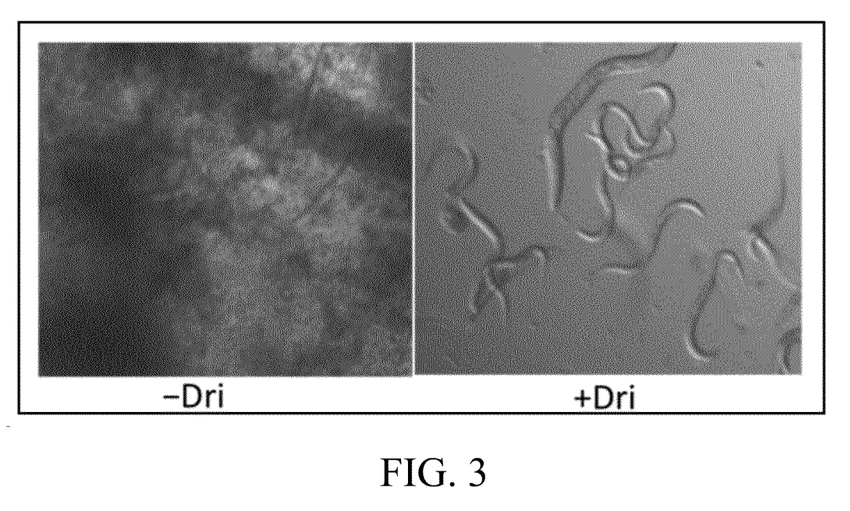
FIG. 3 is a photograph showing the results of antifungal efficacy trials for worms infected with *C. albicans;*

In order to determine antifungal efficacy and toxicity of albicanol and drimenol simultaneously, *Caenorhabditis elegans* (worm), a non-mammalian host model of Candidiasis was used. Worms fed with *C. albicans* yeast cells were incubated in RPMI medium in the presence or absence of drimenol. After 4-5 days worms were scored for survival under an inverted microscope and images were recorded. The results in FIG. 3 show that drimenol (+Dri) (50 μg/ml) prevented *C. albicans* growth and protected worms from *C. albicans* mediated death as indicated by their movements and curved shapes. Note dead worms (straight shapes) and clusters of fungal growth in wells without drimenol (−Dri). Albicanol also exhibited similar results at 70 μg/ml. Overall, the results suggest that drimenol and albicanol are potent antifungal compounds and exhibit less or no cytotoxicity to worms at concentrations that inhibit fungal growth. Additional experiments performed with human intestine epithelial (Int-407) and monkey kidney cells indicated that they were tolerant to albicanol and drimenol up to 375 μM or 75 μg/ml.

We claim:

1. A method for treating a fungal infection in an animal or human body comprising the step of administering to said animal or human body a composition comprising a therapeutically effective amount of one or more drimane derivatives, wherein said drimane derivatives are selected from the group consisting of:

wherein $R^1$ is $CH_2$, CHR', S, NHR', or O,
wherein $R^2$ is OH, OR', =O, $CH_2OH$, CHO, $CO_2H$, $CH=CH_2$, $CH_3$, $CH_2CH_3$, or $C_3H_7$,
wherein $R^3$ is $CH_2OH$, $CH_2NHR'$, NHR', or OR', and
wherein $R^4$ is $CH_2OH$, CHO, $CO_2H$, $CH=CH_2$, $CH_3$, $CH_2CH_3$, $C_3H_7$, or $CH_2NHR'$,
wherein R' is alkyl or aryl.

2. The method according to claim 1, wherein said one or more drimane derivatives are dispersed in a pharamaceutically acceptable carrier.

3. The method according to claim 2, wherein said pharmaceutically acceptable carrier comprises an adjuvant, solvent, or co-solvent to assist said one or more drimane derivatives with penetrating the outer dermal layers of said animal or human skin.

4. The method according to claim 1, wherein said one or more drimane derivatives are present in said composition at a level of at least 0.0003% by weight.

5. The method according to claim 4, wherein said one or more drimane derivatives are present in said composition at a level of between about 0.0003% to about 5% by weight.

6. The method according to claim 1, wherein said composition is applied topically to a portion of said animal or human body afflicted with said fungal infection.

7. The method according to claim 6, wherein said fungal infection is caused by a pathogenic fungus selected from the group consisting of *Candida* spp., *Cryptococcus* spp., *Aspergillus* spp., and dermatophytes.

8. The method according to claim 7, wherein said fungal infection is caused by a member selected from the group consisting of *C. albicans, C. glabrata, C. krusei, C. tropicalis, C. parapsilosis, Cryp. neoformans, A. fumigatus, A. nidulans, A. flavus, Trichophyton equinum, T. tonsurans, Microsporum gypseum* and *M. cani*.

* * * * *